US007922763B2

(12) United States Patent
Song (10) Patent No.: US 7,922,763 B2
(45) Date of Patent: Apr. 12, 2011

(54) APPARATUS FOR RESTORING AORTIC VALVE AND TREATMENT METHOD USING THEREOF

(75) Inventor: Meong-Gun Song, Seoul (KR)

(73) Assignee: Sciencity Co., Ltd., Kangwon-Du (KR)

( * ) Notice: Subject to any disclaimer, the term of this patent is extended or adjusted under 35 U.S.C. 154(b) by 223 days.

(21) Appl. No.: 10/508,746

(22) PCT Filed: Mar. 26, 2004

(86) PCT No.: PCT/KR2004/000694
§ 371 (c)(1),
(2), (4) Date: Mar. 19, 2005

(87) PCT Pub. No.: WO2004/084770
PCT Pub. Date: Oct. 7, 2004

(65) Prior Publication Data
US 2005/0165478 A1 Jul. 28, 2005

(30) Foreign Application Priority Data

Mar. 28, 2003 (KR) .................. 10-2003-0019715

(51) Int. Cl.
*A61F 2/24* (2006.01)
(52) U.S. Cl. .................................. 623/2.36
(58) Field of Classification Search ........ 623/2.36–2.42, 623/903, 1.1, 2.1, 900, 921, 922; 606/140, 606/141, 151, 153, 157, 158; 600/37
See application file for complete search history.

(56) References Cited

U.S. PATENT DOCUMENTS

| 4,190,909 | A | * | 3/1980 | Ablaza | 623/1.32 |
|---|---|---|---|---|---|
| 5,584,879 | A | | 12/1996 | Reimold et al. | |
| 5,674,280 | A | | 10/1997 | Davidson et al. | 623/2 |
| 5,716,397 | A | | 2/1998 | Myers | |
| 6,248,116 | B1 | * | 6/2001 | Chevillon et al. | 606/139 |
| 6,250,308 | B1 | | 6/2001 | Cox | 128/898 |
| 6,264,691 | B1 | * | 7/2001 | Gabbay | 623/2.14 |
| 6,511,506 | B2 | * | 1/2003 | Chevillon et al. | 623/1.36 |
| 7,018,404 | B2 | * | 3/2006 | Holmberg et al. | 623/1.26 |
| 2002/0082684 | A1 | * | 6/2002 | Mishaly | 623/1.36 |
| 2002/0099439 | A1 | * | 7/2002 | Schwartz et al. | 623/1.24 |
| 2003/0033005 | A1 | * | 2/2003 | Houser et al. | 623/1.35 |
| 2003/0069593 | A1 | * | 4/2003 | Tremulis et al. | 606/142 |

(Continued)

FOREIGN PATENT DOCUMENTS

CN 1391453 A 1/2003

(Continued)

OTHER PUBLICATIONS

European Supplementary Search Report dated Nov. 2, 2006, for European Application No. 04723848.0.

(Continued)

*Primary Examiner* — Corrine McDermott
*Assistant Examiner* — Cheryl Miller
(74) *Attorney, Agent, or Firm* — Morrison & Foerster LLP (57) ABSTRACT

The present invention is an apparatus designed to effectuate restoration of normal aortic valvular function where there is aortic valvular regurgitation, either primary or secondary to diseases of the aorta, such as aortic aneurysm, aortic dissection, rheumatic aortic disease, annuloaortic ectasia, etc. are present. The present invention also provides methods of using the apparatus to treat conditions of abnormal aortic valvular function.

8 Claims, 10 Drawing Sheets

U.S. PATENT DOCUMENTS

| | | | | |
|---|---|---|---|---|
| 2004/0230209 | A1* | 11/2004 | Masroor | 606/153 |
| 2005/0065597 | A1* | 3/2005 | Lansac | 623/2.11 |
| 2007/0016290 | A1* | 1/2007 | Duran | 623/2.18 |

FOREIGN PATENT DOCUMENTS

| | | | |
|---|---|---|---|
| JP | 2002-541914 A | | 12/2002 |
| KR | 00190955 B1 | | 1/1999 |
| WO | WO-00/62715 A1 | | 10/2000 |
| WO | WO-01/19292 A1 | | 3/2001 |
| WO | WO 01/78625 A1 | | 10/2001 |
| WO | WO 02/03892 | * | 1/2002 |
| WO | WO/02/03892 | | 1/2002 |
| WO | WO/03/020179 | | 3/2003 |

OTHER PUBLICATIONS

Al Fagih, M.R. (Nov. 1988). "Aortic Valve Repair Using Bovine Pericardium for Cusp Extension," *J. Thorac. Cardiovasc. Surg.* 96(5):760-764.

Cosgrove, D.M. et al. (Oct. 1991). "Valvuloplasty for Aortic Insufficiency," *J. Thorac. Cardiovasc. Surg.* 102(4):571-577.

David, T.E. (1994). "Aortic Valve Repair in Patients with Marfan Syndrome and Ascending Aorta Aneurysms Due to Degenerative Disease," *J. Card. Surg.* 9(2 Suppl.):182-187.

Gelsomino, S. et al. (Jun. 2003). "A Short-Term Experience with the Tirone David I Valve Sparing Operation for the Treatment of Aneurysms of the Ascending Aorta and Aortic Root," *Cardiovascular Surgey* 11(3):189-194.

Haydar, H.S. et al. (1997). "Valve Repair for Aortic Insufficiency: Surgical Classification and Techniques," *Eur. J. Cardiotrhorac. Surg.* 11(2):258-265.

International Search Report dated Jul. 26, 2004, for Application PCT/KR2004/000694, filed Mar. 26, 2004, 3 pages.

Kallenbach, K. et al. (2002). "Results of Valve-Sparing Aortic Root Reconstruction in 158 Consecutive Patients," *Ann. Thorac. Surg.* 74(6):2026-2033.

Non-Final Office Action mailed on Sep. 15, 2010, for U.S. Appl. No. 12/205,115, filed Sep. 5, 2008, 7 pages.

Written Opinion dated Jul. 26, 2004, for Application PCT/KR2004/000694, filed Mar. 26, 2004, 5 pages.

\* cited by examiner

APPARATUS FOR RESTORING AORTIC VALVE AND TREATMENT METHOD USING THEREOF

TECHNICAL FIELD

The present invention relates, in general, to an apparatus for restoring aortic valve and, more particularly, to an apparatus for restoring aortic valve which is designed to effectuate restoration of normal aortic valvular function where aortic valvular regurgitation either primary or secondary to diseases of the aorta such as aortic aneurysm, aortic dissection, rheumatic aortic disease annuloaortic ectasia and etc. is present.

BACKGROUND ART

The heart has four valves which ensure forward flow of incoming blood to the systemic circulation. The left side has the mitral valve which is positioned between the left atrium and left ventricle and the aortic valve which is located at the junction of the left ventricular outflow tract and the aortic root. The function of these two valves is to ensure that oxygenated blood from the lung continues to flow into aortic root through the left side of the heart in a forward direction. In the right side of the heart, there are two similar valves called the tricuspid valve and the pulmonary valve.

These four valves are entirely passive structures which neither consume energy nor contract dynamically. These valves are composed of leaflets which passively open and close dictated by the pressure difference created. The mitral and tricuspid valves are called atrioventricular valves since they are located between atrium and ventricle. The mitral valve is composed of two leaflets and the tricuspid valve is composed of three leaflets. The aortic and pulmonary valves are called semilunar cusps since the leaflets are semilunar in shape. Both of the aortic and pulmonary valves have three cusps.

Heart valves may be affected by abnormality in structure and function by congenital or acquired valve disorder. Congenital valve abnormalities may either manifest with life-threatening disorder at birth or remain latent until mid life or even later in life. Acquired disorders are frequently caused by conditions such as rheumatic fever, degenerative disorder, infection or trauma.

Severe aortic regurgitation may be caused by aortic dissection, in which case aortic valve replacement is usually required. In addition, serious aortic regurgitation may also occur as a result of rheumatic or degenerative valvular disease. The mainstay of prosthetic valves used in aortic valve disease is so called mechanical valve and tissue valves, both of the stented type. The leaflets of mechanical valves are constructed of pyrolitic carbon material encased in a titanium housing. Tissue valves are composed of materials derived from animal tissue. Tissue valves are commonly constructed over a skeletal frame of titanium with an outer sewing rim to facilitate suture implantation. The valve material per se may either come from bovine pericardium or from the porcine aortic valve treated in glutaraldehyde. These prosthetic apparatus are implanted in the patients' aortic annulus after the diseased aortic leaflets have been removed.

To prevent thrombotic complications after a mechanical valve implantation, lifelong anticoagulation is essential. Even with anticoagulation, patients could still experience bleeding or thrombotic complications. On the other hand, tissue valves are generally free of such complications, obviating anticoagulation, but tissue valves have relatively limited durability compared to mechanical valves. As a result these patients require future reoperation. To overcome the limitations of these different types of artificial valves, a durable method of aortic valve restoration is desirable. However, at present aortic valve repair is considered feasible in only certain selected situations.

The aortic root not only serves as a simple passage for blood, but it is also a highly sophisticated elastic structure which allow cyclic expansion of the aortic diameter to as much as 30% of its basal diameter according to the rhythmic changes of the cardiac cycle. Since this structure is sustained under very high blood pressures, most of the existing methods of aortic valve repair unable to withstand the associated mechanical stress are prone to failure and relapse.

The three major factors to preserve the function of the aortic valve include maintaining the appropriate diameter of the sinotubular junction and the aortic annulus, and state of the leaflets per se. Only when the functions of these three factors are optimally recovered, the aortic valve function can be successfully restored. Existing methods to repair the aortic valve haven't met these requirements entirely. For example, resuspension of the aortic valve leaflets inside an artificial vascular conduit has been suggested as an effective method of repairing ascending aortic aneurysm due to Marfan syndrome with morphologically normal aortic leaflets (David T. E. 'Aortic valve repair in patients with Marfan syndrome and ascending aorta aneurysms due to degenerative disease' J. Card. Surg. 1994; 9(2 Suppl): 182-7). However, this method is applicable only to limited situations. One drawback is that the sinus portion in the proximal aortic root has to be removed. Furthermore, this method may lead to serious bleeding complications in aortic dissection as sutures are passed through friable and edematous tissue.

Another surgical method applicable to Marfan patients, is replacement of aneurysmal ascending aortic tissue with a suitably tailored segment of a vascular conduit (Sndro Gelsomino et al. 'A short-term experience with the Tirone David I valve sparing operation for the treatment of aneurysms of the ascending aorta and aortic root' Cardiovascular Surgery 2003; 11(3): 189-194; Kallenbach K. et al. 'Results of valve-sparing aortic root reconstruction in 158 consecutive patients' Ann. Thorac. Surg. 2002; 74(6): 2026-32). However, this method is also prone to serious bleeding in aortic dissection or even in simple aneurysms in these patients. Furthermore, this method also shares the same drawback having to remove the function of the native sinus of Valsalva.

In contrast to these methods, replacement of the dysfunctional valve leaflets with glutaraldehyde fixed autologous pericardium may appear to correct the problem of aortic regurgitation (Riyadh Cardiac Centre, Armed Forces Hospital, Kingdom of Saudi Arabia. 'Aortic valve repair using bovine pericardium for cusp extension' J. Thorac. Cardiovasc. Surg. 1988; 96(5): 760-4; Cosgrove D. M. et al. 'Valvuloplasty for aortic insufficiency' J. Thorac. Cardiovasc. Surg. 1991; 102(4): 571-6; Haydar H. S. at al. 'Valve repair for aortic insufficiency: surgical classification and techniques' Eur. J. Cardiothorac. Surg. 1997; 11(2): 258-65), but in the long term, leaflet coaptation will eventually fail as this function is dictated by the diameters of the sinotubular junction and the aortic annulus, both of which may progressively increase.

DISCLOSURE OF INVENTION

The present invention has been devised with the aims of addressing the above problems, while at the same time restoring the normal functioning of the aortic valve by affecting not only the aortic leaflets but also the surrounding structures comprising the aortic root.

In order to accomplish the above objectives, the present invention provides an apparatus composed of (1) a band type annulus inner stabilizer (sometimes ring type annulus inner stabilizer) which is implanted in the endoluminal aspect of the aortic lumen to fix the aortic annular diameter and (2) an annulus outer felt stabilizer which is implanted on the outside surface of aorta to support the inner stabilizer.

In addition, the present invention provides an apparatus for restoring the sinotubular junction(STJ) in the ascending aorta composed of (1) a ring type STJ inner stabilizer which is implanted in the sinotubular junction in the ascending aorta and (2) a ring type STJ outer felt stabilizer which is implanted on the outside surface of the sinotubular junction to support the inner stabilizer.

BEST MODE FOR CARRYING OUT THE INVENTION

The apparatus according to the present invention is used for the treatment of simple aortic regurgitation or aortic regurgitation derived from aortic dissection or aortic regurgitation accompanied by ascending aortic aneurysm or annuloaortic ectasia etc. By fixing the diameter of the aortic annulus and the sinotubular junction, the apparatus of the present invention is able to provide effective repair of aortic regurgitation.

Aortic regurgitation is caused among other causes by increase in diameter of the sinotubular junction(STJ), increase in diameter of the aortic annulus, and degeneration of the aortic leaflets. In case of aortic regurgitation caused by increase in aortic annular diameter and STJ, aortic regurgitation may be effectively corrected by normalizing the diameters in STJ and aortic annular diameters.

Figure 1A:
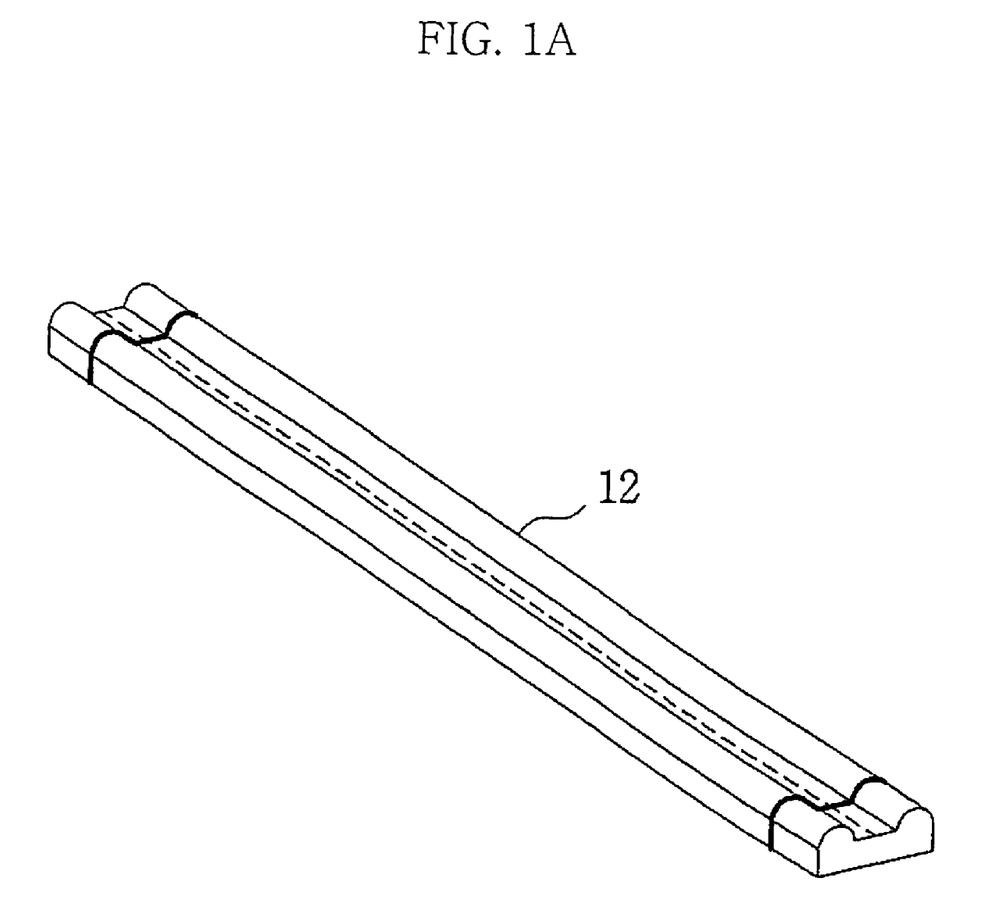
FIG. 1a is perspective view of the aortic annulus inner stabilizer in band type according to the present invention.
Figure 1B:
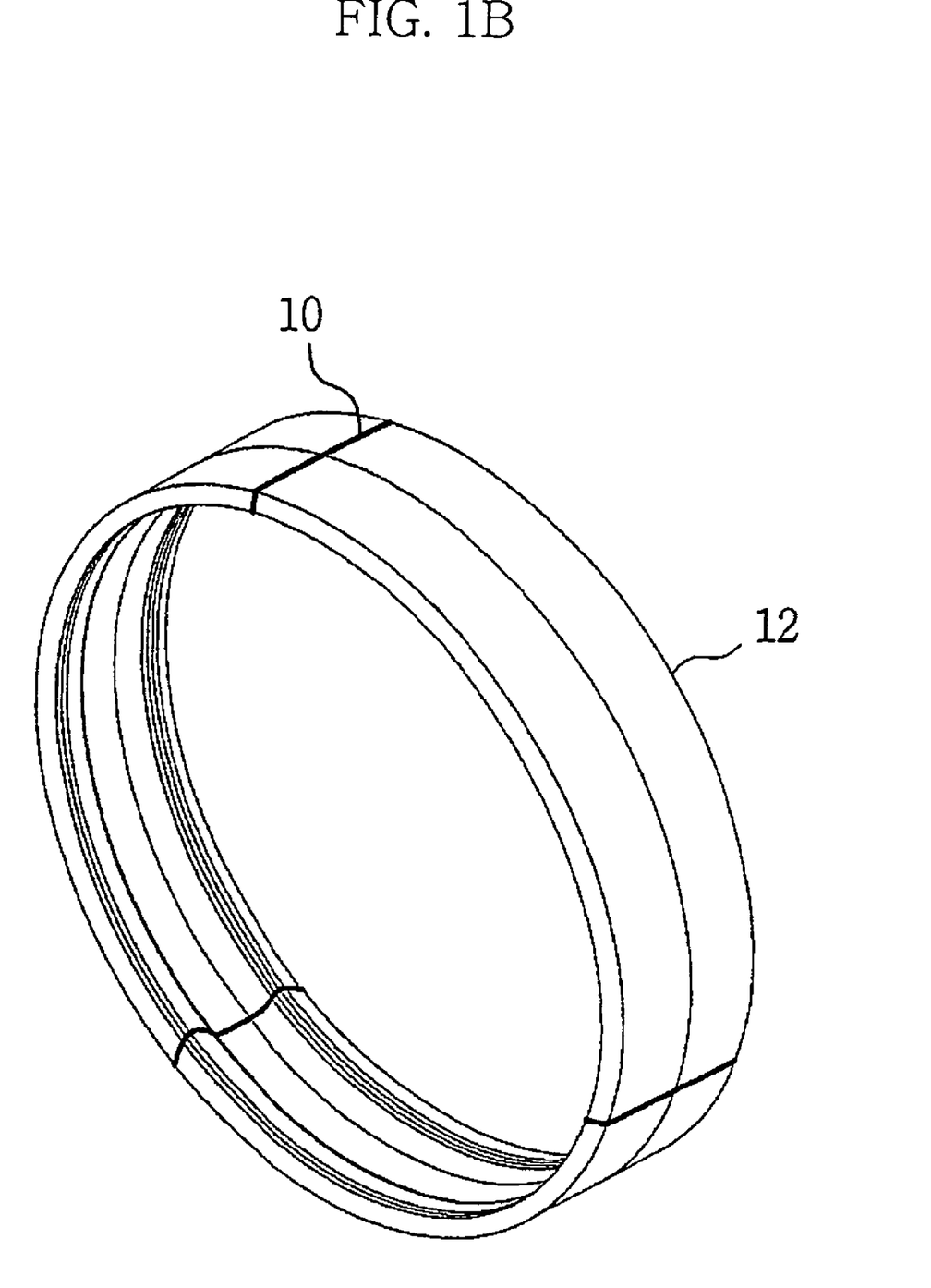
FIG. 1b is perspective view of the aortic annulus inner stabilizer in ring type according to the present invention.
Figure 1C:
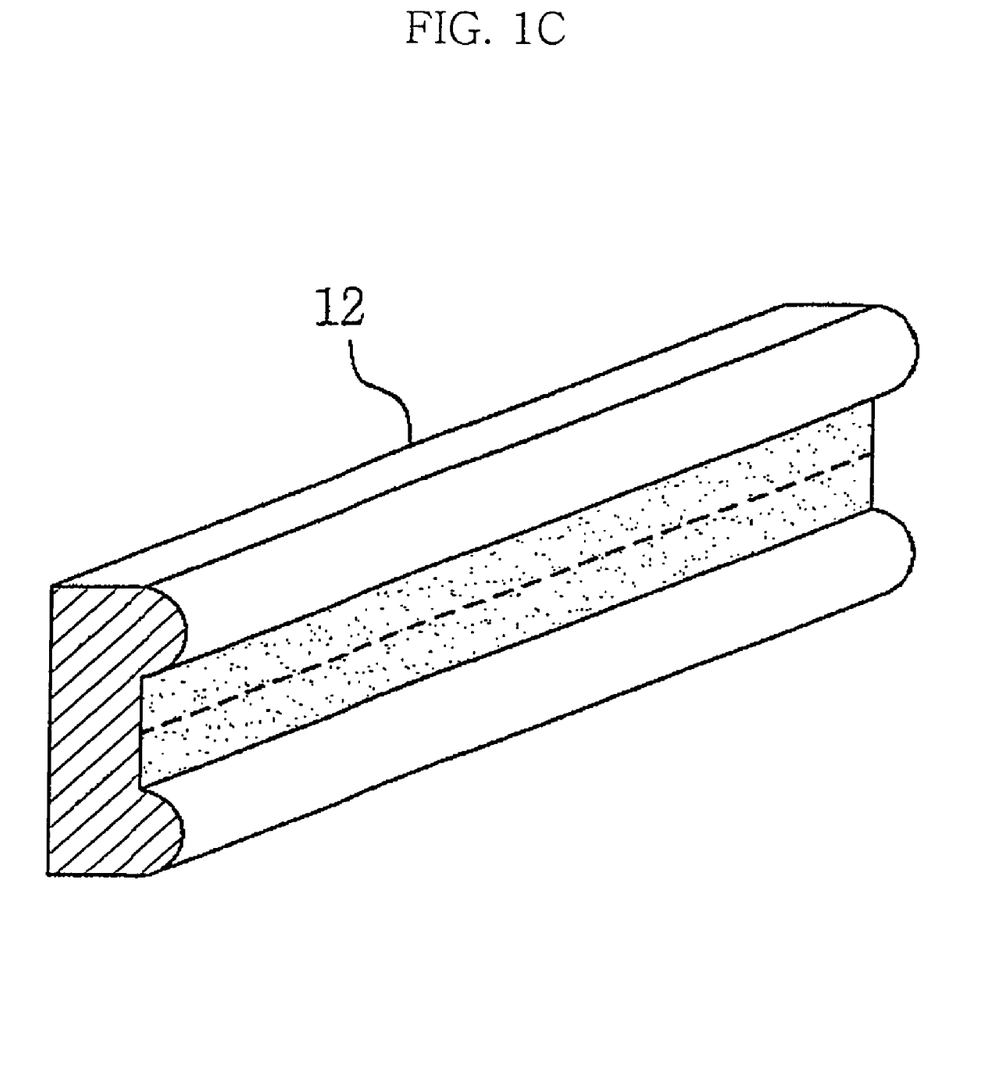
FIG. 1c is cross sectional view of the aortic annulus inner stabilizer in band type or in ring type according to the present invention.
Figure 3A:
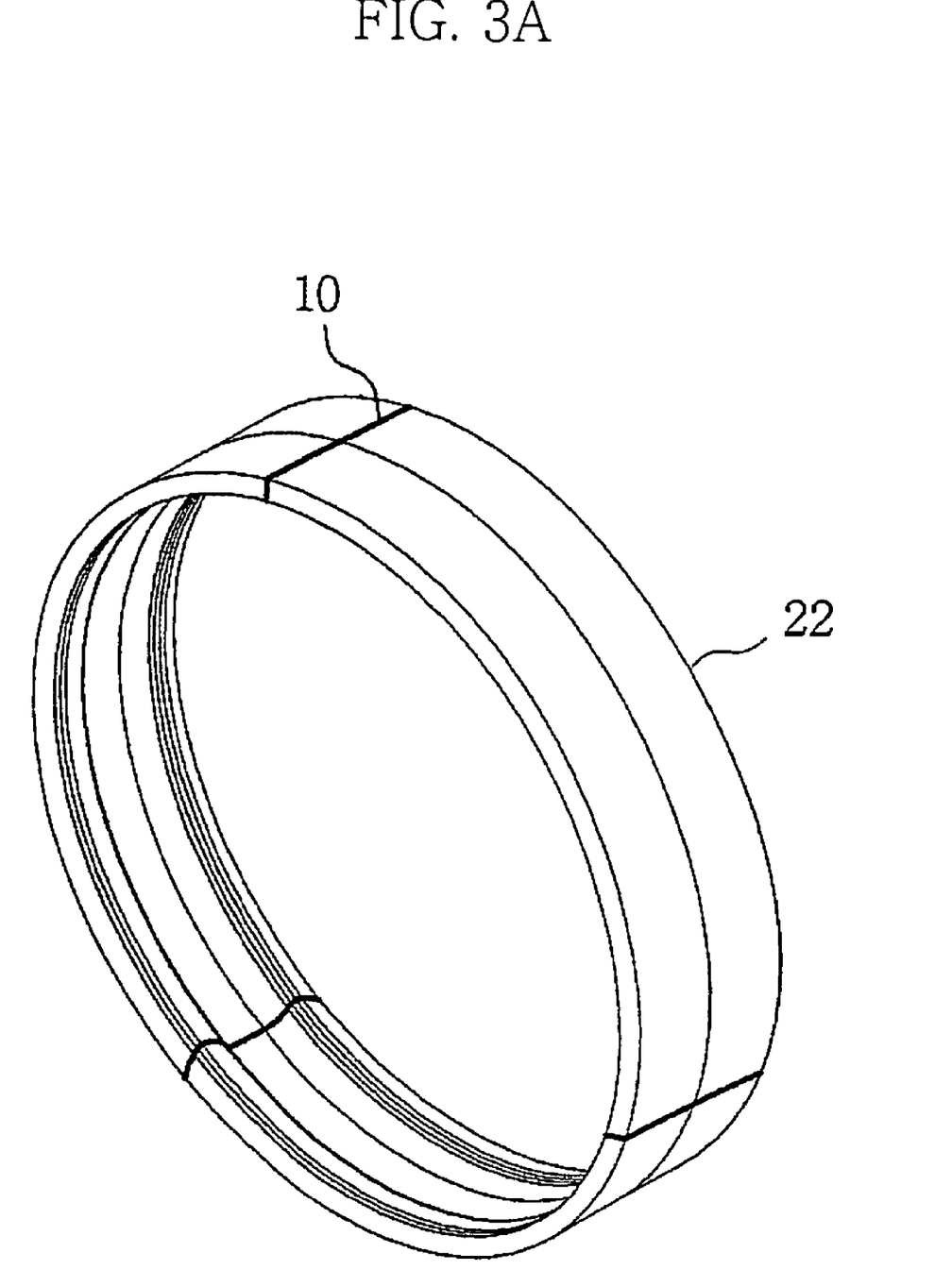
FIG. 3a is perspective view of the sinotubular junction (STJ) inner stabilizer in ring type according to the present invention.
Figure 3B:
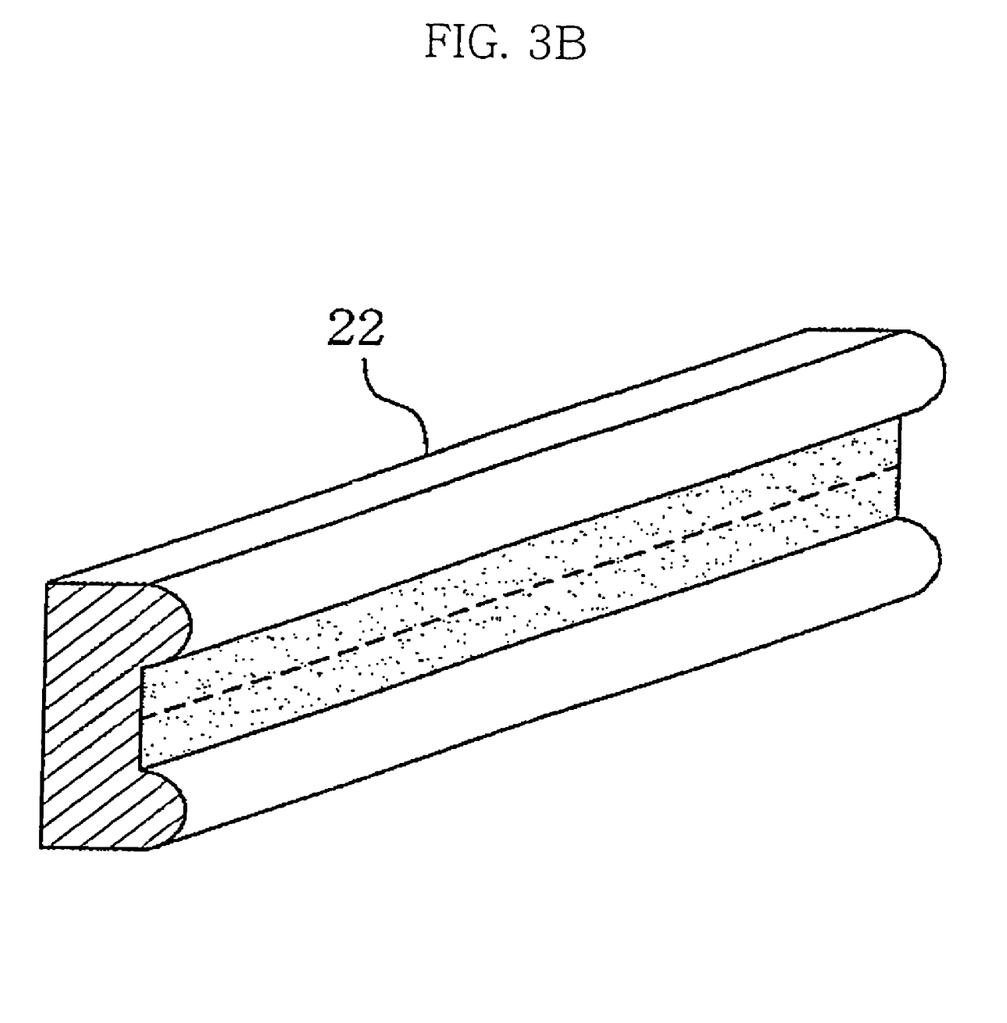
FIG. 3b is cross sectional view of the sinotubular junction (STJ) inner stabilizer in ring type according to the present invention.
Figure 4:
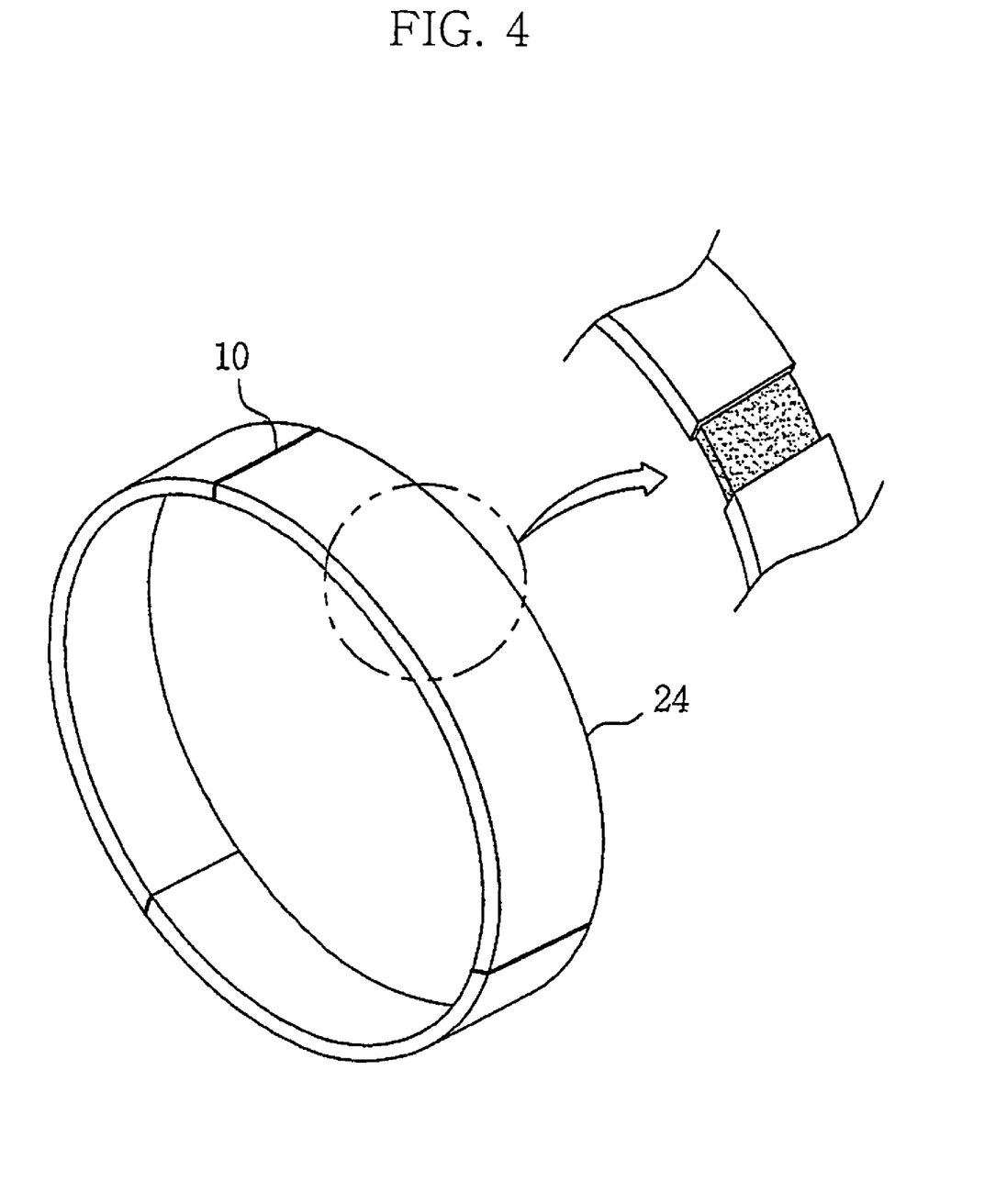
FIG. 4 is perspective view of the sinotubular junction(STJ) outer felt stabilizer in ring type according to the present invention and interior view of the outer felt stabilizer.

Hereinafter, the preferred embodiments of the present invention will be described in detail with reference to the attached drawings, in which:

FIG. 1a is a perspective view of the aortic annulus inner stabilizer in band type according to the present invention; FIG. 1b is a perspective view of the aortic annulus inner stabilizer in ring type according to the present invention; FIG. 1c is a sectional view of the aortic annulus inner stabilizer in band or ring type according to the present invention; FIG. 2a is a perspective view of the aortic annulus outer felt stabilizer in band type according to the present invention; FIG. 3a is a perspective view of the STJ inner stabilizer in ring type according to the present invention; FIG. 3b is a sectional view of the STJ inner stabilizer in ring type according to the present invention; FIG. 4 is a perspective view of the STJ outer felt stabilizer in ring type according to the present invention and interior view of the outer felt stabilizer.

The aortic valve repair apparatus according to the present invention comprise (1) a component to maintain the constant diameter of the aortic annulus and (2) another component to maintain the constant diameter of the sinotubular junction. Each of these components is composed of (1) an inner stabilizer which sustains the diameter from inside of the aortic lumen and (2) an outer stabilizer designed to support the inner stabilizer from outside of the aortic lumen.

Figure 2:
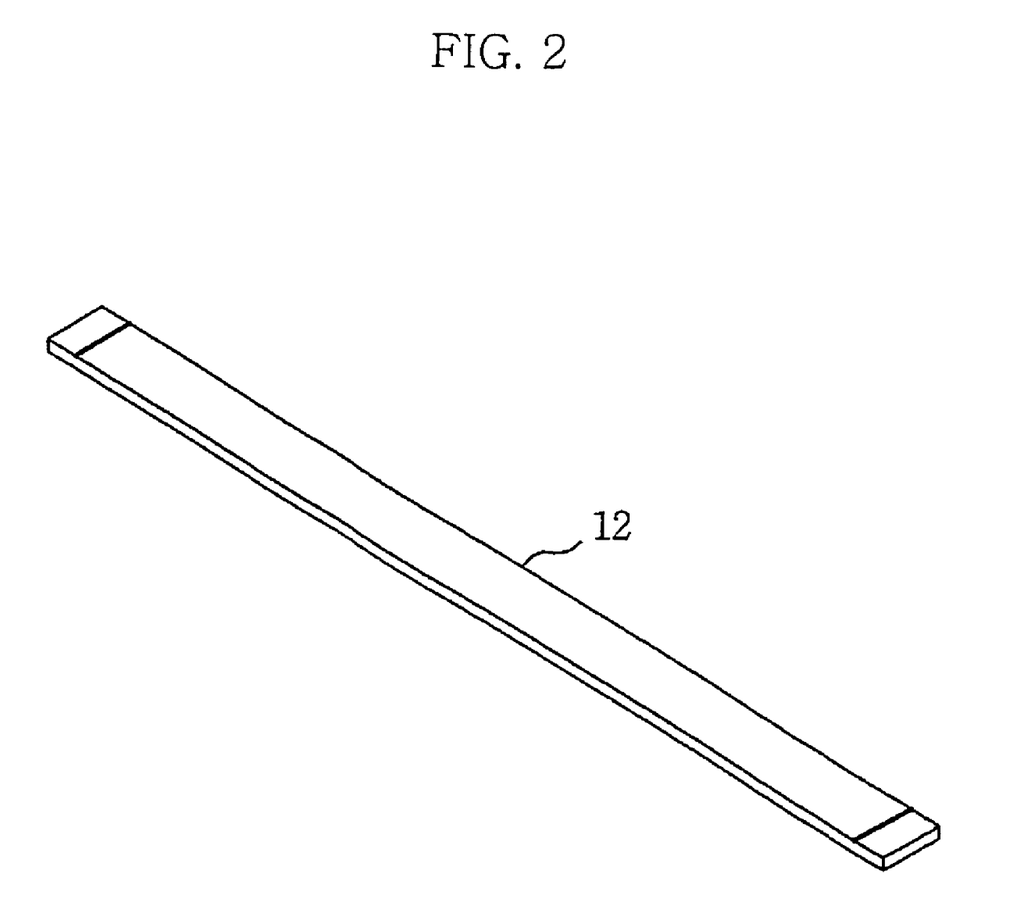
FIG. 2a is perspective view of the annulus outer felt stabilizer in band type according to the present invention.

According to FIGS. 1 and 2, the apparatus for aortic annular repair is composed of an inner band or ring type stabilizer (12) which in effect determines the annular diameter from luminal aspect of the aorta and outer band type felt stabilizer (14) which supports the inner stabilizer from adventitial surface of the aorta.

The above annulus inner stabilizer (12), which is designed to maintain a constant aortic annular diameter, is constructed of a flexible band shaped structure with the purpose of fixing only the fibrous portion of the aortic annulus exclusive of the muscular portion. However, with enlargement of the muscular portion of the aortic annulus, a ring type annulus inner stabilizer may be required to fix the aortic annulus in a circumferential fashion.

Furthermore, to allow ease of suture passage and tighter apposition between the annulus inner stabilizer and luminal surface of the aortic wall, that portion of the stabilizer where suture is to be passed is made thinner than the surrounding parts of the stabilizer and marked with centrally dotted line (FIGS. 1c, 3b). Every one third (10) of the circumference of the ring type stabilizer is marked to facilitate the correct orientation (FIGS. 1b, 3a). As the band type stabilizer is designed to fix only the fibrous portion of the aortic annulus while allowing free movement to the muscular portion, the length of the band is marked so that it may extend a further about 2 mm beyond the extent of the fibrous portion of the aortic annulus at both ends (FIG. 1a) to facilitate implantation.

The annulus outer felt stabilizer (14) which is placed on the outside surface of the aortic wall, is paired with the annulus inner stabilizer (12) to fix diameter of the aortic annulus consistently while supporting the inner stabilizer. The annulus outer stabilizer is marked vertically about 2 mm away from its both ends (FIG. 2).

The annulus inner stabilizer (12) and outer felt stabilizer (14) is made of any biologically inert materials such as polyester, polytetrafluoroethylene, and other types of synthetic fibers including polyamide, polyacrylonitrile, polyvinylalcohol, polyurethane, polypropylene etc.

According to FIGS. 3 and 4, the STJ repair apparatus consist of ring type STJ inner stabilizer (22) designed to fix the diameter of the STJ from the luminal surface of the aorta and ring type STJ outer felt stabilizer (24) supporting the inner stabilizer from outside of sinotubular junction(STJ) of the ascending aorta. The STJ repair apparatus is available only as a ring type and provides structural support to the aorta from both the inside and outside of the aortic wall at the STJ level.

The STJ inner stabilizer (22) is made of any synthetic fiber or biological material having elasticity. Like the annulus inner stabilizer (12), the part of the STJ inner stabilizer where the needle is to be passed is made thinner than the surrounding part of the ring to ensure tight apposition to the aortic wall (FIG. 3b). The above thin portion has dotted marks centrally for allowing easy and correct suture. Furthermore, every one third (10) of the ring type STJ inner stabilizer along its circumference is clearly marked vertically (FIG. 3a).

The outer felt stabilizer of the STJ repair apparatus (24) is paired with the inner stabilizer (22) and is designed to fix the diameter of the STJ constantly. It is implanted at the STJ onto the outer wall of the aorta. Like the STJ inner stabilizer, every one third (10) of the circumference is marked in identical way to the inner stabilizer (FIG. 4). The STJ outer felt stabilizer can be covered with any other synthetic fiver or biological material to prevent severe adhesion to the surrounding tissues.

The surgical technique using aortic valve repair apparatus according to the present invention is as follows:

To correct aortic regurgitation secondary to increased diameter of the aortic annulus, a ring or band type stabilizer aimed to decrease the aortic annulus diameter to the desired dimension is implanted in the aortic annulus serving as the inner stabilizer (12). The band type annulus outer stabilizer is placed on the corresponding outside aortic wall to structurally support. These two stabilizers implanted on both the inside and outside surfaces of the aortic annulus, decrease the diameter of aortic annulus to the desired dimension and thereby effectively correct aortic regurgitation.

In similar fashion, a STJ inner stabilizer (22) is implanted in the aortic true lumen at the STJ of ascending aorta. A STJ outer stabilizer (24) is implanted on the outside surface of the aorta at the STJ to reinforce the STJ inner stabilizer (22). The implantation of these two STJ stabilizers may effectively correct aortic regurgitation by normalizing the aortic diameter at the sinutubular junction.

Where abnormal enlargement has occurred at both the annulus and STJ levels, aortic regurgitation may be corrected by repairing the aortic root at both of these levels as described. Furthermore, securing repair of the aortic root at both of these levels may effectively prevent recurrence of aortic regurgitation resulting from the dilatation of the untreated component.

Aortic regurgitation caused by several diseases can be corrected by the aortic valve and root preserving method described hereinafter. The corrective procedure of the present invention may vary depending on the cause of aortic regurgitation. In case of ascending aortic aneurysm without annuloaortic ectasia or aortic dissection, the corrective procedure is implemented by implanting one pair of ring type aortic stabilizer at the ascending aortic sinotubular junction level only.

However, in case of an annuloaortic ectasia (for example, a Marfan syndrome) accompanied by ascending aortic aneurysm and severe aortic regurgitation, the corrective procedure is implemented not only by implanting one pair of ring type stabilizer in ascending aortic sinotubular junction level but also by implanting another pair of band type stabilizer at the aortic annular level simultaneously.

Figure 5A:
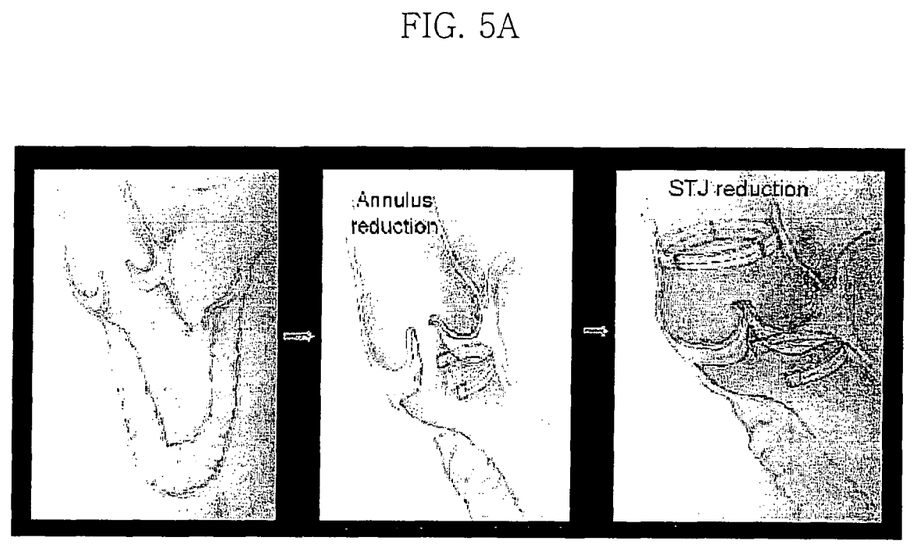
FIG. 5a is a schematic demonstration of surgical implantation technique using the apparatus according to the present invention.

Based on the above description, the corrective procedure may be divided into two parts (FIG. 5a); surgical implantation technique of the band type stabilizer in the aortic annular level and surgical implantation technique of the ring type stabilizer in STJ level.

Figure 5B:
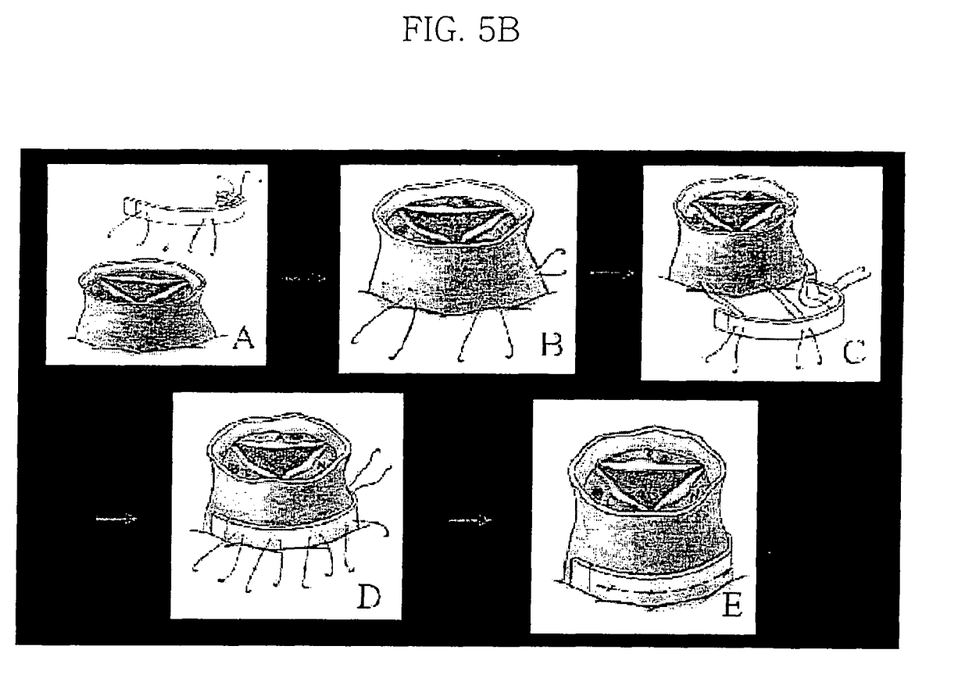
FIG. 5b is schematic demonstration of implantation procedure of the band type stabilizer in aortic annulus level.

A. Surgical Technique—Implantation Procedure of the Band Type Stabilizer in Aortic Annulus Level (FIG. 5b)

The annulus repairing apparatus is composed of band type inner and outer stabilizer which have some elasticity. The annulus inner stabilizer is implanted at the fibrous portion of the left ventricular outflow tract just inferior to the aortic valve leaflets. The annulus outer stabilizer is implanted at the corresponding side of the aorta on the outside aspect of the aortic annulus thereby sandwiching the involved portion of the aortic wall between the two strips of ring material.

The ideal size of band type annulus inner stabilizer is determined by two factors; (1) measuring the length of the muscular portion of the left ventricular outflow tract which is relatively constant and (2) measuring the actual aortic valve surface area. This length approximates a half of the aortic annulus. The selected annulus inner band type stabilizer is then apposed to the fibrous portion of the aortic annulus as described above. One arm of a double-armed about 17 mm #3-0 polypropylene suture is passed through one end of the annulus inner stabilizer. It is then passed through the annulus at the fibromuscular junction under the left coronary cusp. The other arm of the polypropylene suture is then passed through the annulus inner stabilizer spaced about 5 mm away horizontally. The suture is passed through the stabilizer and annulus in identical way to complete a horizontal mattress suture.

An additional 4 or 5 horizontal mattress sutures are placed as needed in like manner to completely appose the annulus inner stabilizer against the luminal surface of the fibrous portion of the aortic annulus. Once all of the above sutures have been completed, the outer band stabilizer is implanted. The corresponding outer band stabilizer is measured against the external surface of the aortic annulus through which the horizontal mattress polypropylene sutures have been placed. Each arm of the polypropylene horizontal mattress sutures is passed through the respective sites of the annulus outer band stabilizer. Once all arms of the sutures are passed, the needles are cut and tied to secure fixation of the inside and outside stabilizer to the aortic annulus and aortic wall.

Figure 5C:
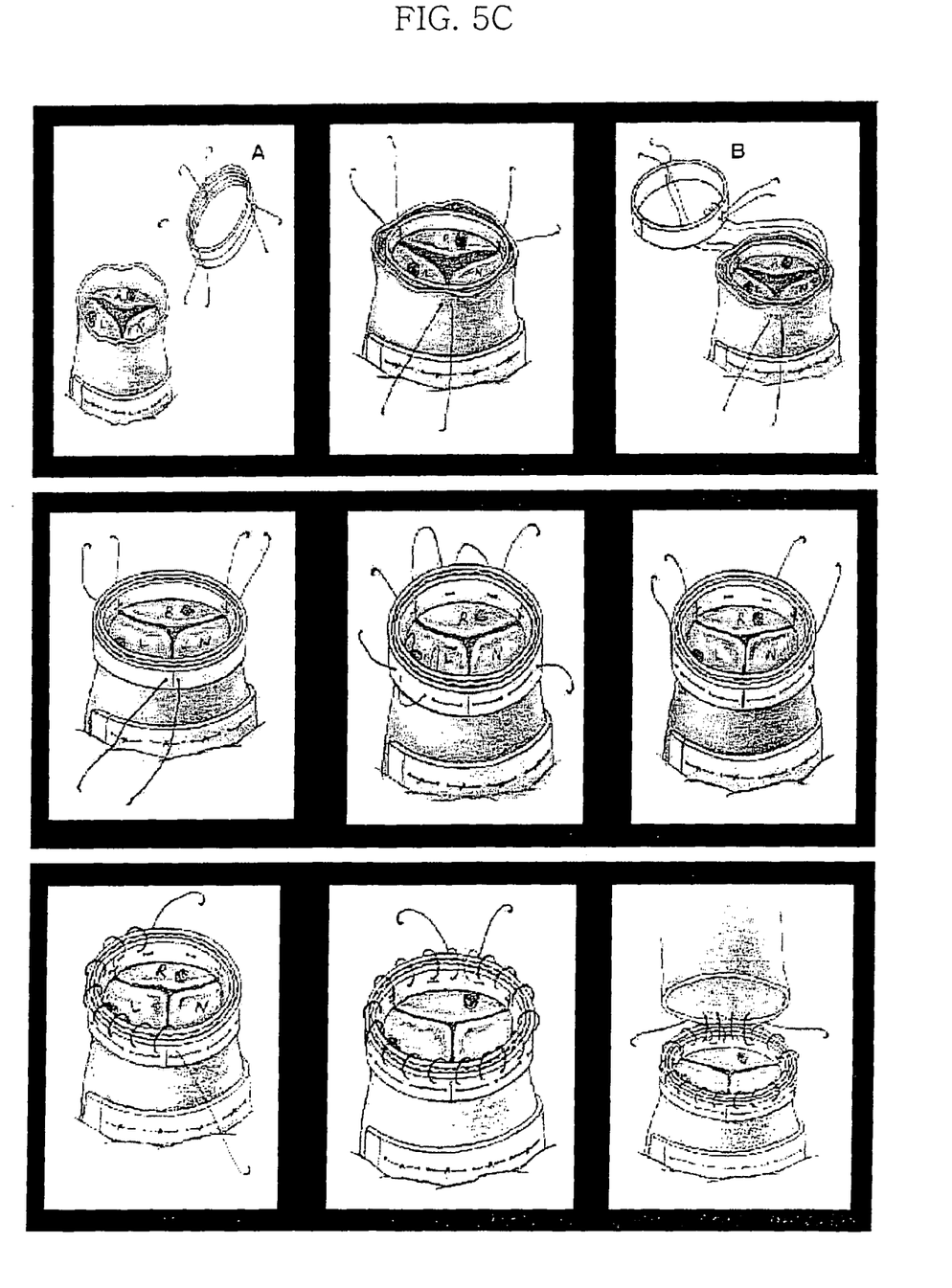
FIG. 5c is schematic demonstration of implantation procedure of ring type stabilizer in STJ level.

B. Surgical Technique—Implantation Procedure of Ring Type Stabilizer in STJ Level (FIG. 5c)

The STJ stabilizing apparatus consists of an inner and outer ring stabilizer. The STJ inner stabilizer is designed to normalize the aortic diameters at the level of the sinotubular junction. Determination of the ideal size of STJ inner stabilizer is based on the length of muscular portion of aortic annulus and the aortic valve surface area. The normal aortic root configuration is cone shaped such that the diameter at the sinotubular junction is approximating 10 to 20% less than that of the base dimension.

Every one third (10) of the circumference of the ring type STJ inner stabilizer is clearly marked for easy orientation. Each mark (10) is meant to correspond to each of the commissures of the aortic leaflets, assuming for simplification that each of the commissures is located at each third of the circumference of the aortic circumference. The repair is initiated by passing a horizontal mattress suture with a double-armed #4-0 polypropylene suture in the STJ inner stabilizer at each marking so that three equidistant horizontal mattress sutures are placed. Each arm of the suture that is passed through the STJ inner stabilizer is then successively passed through the aortic wall at the level of the commissures. This procedure is repeated for the remaining commissures.

The respective arms of the three pairs of sutures that have passed the aortic wall at the commissural level are then passed through the STJ outer ring stabilizer. And the two arms of the polypropylene sutures are tied together without cutting the needles at each commissure.

Once these ties are completed, the STJ inner and outer ring stabilizers at these three points are apposed to the intimal and adventitial surfaces of the aorta, respectively. Starting from the commissure between the non-coronary and the left coronary cusp, one arm of the polypropylene suture is used to carry out a continuous horizontal mattress suture along the entire circumference of the aorta. The sutures are placed so that the needle passes all three outer ring, aortic wall, and the inner ring complex.

After the continuous horizontal mattress suture has spanned the circumference of the aorta, the two arms of the polypropylene suture are tied again. By tying the two arms, the first phase of the STJ stabilizer implantation is completed. After tying only the needle attached to the arm of the polypropylene suture that was used to complete the horizontal mattress suture is cut whereas the needle attached to the arm not used in the horizontal mattress suture is left in place. This arm of the polypropylene suture is used to reinforce the initial horizontal mattress suture with a running continuous over and over suture starting from where the tie was made. This running suture which serves to strengthen the hemostasis and reinforce the initial apposition of the stabilizer runs the entire circumference of the aorta.

Once completed, the arm of this suture is also tied together with the arm of the polypropylene suture that was used earlier to make the initial horizontal mattress suture. The completed repair results in a firmly reinforced resected margin of the ascending aorta at the level of the sinotubular junction. The luminal aspect of the implanted STJ inner stabilizer should be carefully inspected to ensure that the coronary ostia are free of any significant encroachment by the stabilizer. Then the distal ascending aorta is sutured over the proximally repaired end of STJ in the usual manner with a continuous running suture of polypropylene. In case that the distal ascending aorta is replaced with the graft, the conduit is sutured to the above proximally repaired aortic end.

The advantage of preserving the functionality of the aortic valve in this manner include standardization of the surgical technique as described above. The sinus structures are preserved, thereby optimizing leaflet function and stress distribution. Favorable long-term results may therefore be anticipated such as minimization of damage to the native aortic leaflets. A further advantage in preserving the native sinuses include a more streamlined and less turbulent flow through aortic valve and the respective sinuses.

What is claimed is:

1. A treatment method for aortic valvular regurgitation associated with an aortic valve having an aortic annulus, an aortic lumen and a sinotubular junction, comprising:
   implanting an inner discontinuous band stabilizer inside the aortic lumen along an interior surface of the aortic annulus of the aortic valve,
   implanting an outer discontinuous band stabilizer outside the aortic lumen along an exterior surface of the aortic annulus of the aortic valve;
   implanting an inner continuous ring stabilizer along an interior surface of the sinotubular junction of the aortic valve; and
   implanting an outer continuous ring stabilizer along an exterior surface of the sinotubular junction of the aortic valve.

2. A treatment method for aortic valvular regurgitation associated with an aortic valve having an aortic annulus, an aortic lumen and a sinotubular junction, comprising:
   implanting an inner discontinuous band stabilizer inside the aortic lumen proximate the aortic annulus of the aortic valve, wherein the inner discontinuous band stabilizer comprises a sewing passage wherein a portion of the inner discontinuous band stabilizer is thinner than surrounding portions of the inner discontinuous band stabilizer;
   implanting an outer discontinuous band stabilizer outside the aortic lumen proximate the aortic annulus of the aortic valve;
   implanting an inner continuous ring stabilizer proximate an interior surface of the sinotubular junction of the aortic valve, wherein the inner continuous ring stabilizer comprises a sewing passage wherein a portion of the inner continuous ring stabilizer is thinner than surrounding portions of the inner continuous ring stabilizer; and
   implanting an outer continuous ring stabilizer proximate an exterior surface of the sinotubular junction of the aortic valve.

3. The treatment method for aortic valvular regurgitation as set forth in claim 2, wherein the outer continuous ring stabilizer comprises three equally spaced markers on its circumference.

4. The treatment method for aortic valvular regurgitation as set forth in claim 2, wherein the outer discontinuous band stabilizer comprises vertical marks about 2 mm from each free end thereof.

5. The treatment method for aortic valvular regurgitation as set forth in claim 2, wherein no graft or prosthetic flexible tubular structure is used between the outer discontinuous band stabilizer and the outer continuous ring stabilizer.

6. The method of claim 2 wherein the outer continuous ring stabilizer, the inner continuous ring stabilizer, the outer discontinuous band stabilizer, and the inner discontinuous band stabilizer each comprise a synthetic fiber.

7. A treatment method for aortic valvular regurgitation associated with an aortic valve having an aortic annulus, an aortic lumen and a sinotubular junction, comprising:
   implanting an inner discontinuous band stabilizer inside the aortic lumen proximate the aortic annulus of the aortic valve;
   implanting an outer discontinuous band stabilizer outside the aortic lumen proximate the aortic annulus of the aortic valve;
   implanting an inner continuous ring stabilizer proximate an interior surface of the sinotubular junction of the aortic valve; and
   implanting an outer continuous ring stabilizer proximate an exterior surface of the sinotubular junction of the aortic valve, wherein the outer continuous ring stabilizer, the inner continuous ring stabilizer, the outer discontinuous band stabilizer, and the inner discontinuous band stabilizer each comprise a synthetic fiber.

8. A treatment method for aortic valvular regurgitation associated with an aortic valve having an aortic annulus, an aortic lumen and a sinotubular junction, comprising:
   implanting an inner discontinuous band stabilizer inside the aortic lumen proximate the aortic annulus of the aortic valve, wherein the inner discontinuous band stabilizer comprises vertical marks about 2 mm from each free end thereof;
   implanting an outer discontinuous band stabilizer outside the aortic lumen proximate the aortic annulus of the aortic valve, wherein the outer discontinuous band stabilizer comprises vertical marks about 2 mm from each free end thereof;
   implanting an inner continuous ring stabilizer proximate an interior surface of the sinotubular junction of the aortic valve; and
   implanting an outer continuous ring stabilizer proximate an exterior surface of the sinotubular junction of the aortic valve.

* * * * *